United States Patent
Schwall et al.

(10) Patent No.: US 6,214,344 B1
(45) Date of Patent: *Apr. 10, 2001

(54) HEPATOCYTE GROWTH FACTOR RECEPTOR ANTAGONISTS AND USES THEREOF

(75) Inventors: Ralph H. Schwall, Pacifica; Kelly Helen Tabor, Hillsborough, both of CA (US)

(73) Assignee: Genetech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/006,776

(22) Filed: Jan. 14, 1998

Related U.S. Application Data

(63) Continuation of application No. 08/459,849, filed on Jun. 2, 1995, now abandoned.

(51) Int. Cl.$^7$ .......................... C07K 16/28; C07K 16/30; A61K 39/395

(52) U.S. Cl. ...................... 424/174.1; 424/130.1; 424/138.1; 424/141.1; 424/143.1; 424/152.1; 424/155.1; 424/172.1; 530/387.7; 530/388.22; 530/388.8; 530/388.85; 530/389.7

(58) Field of Search .................... 424/138.1, 143.1, 424/152.1, 130.1, 141.1, 155.1, 172.1, 174.1; 530/388.8, 388.88, 389.7, 387.7, 388.22

(56) References Cited

U.S. PATENT DOCUMENTS

| | | |
|---|---|---|
| 4,342,566 | 8/1982 | Theofilopoulos et al. |
| 4,816,567 | 3/1989 | Cabilly et al. |
| 5,227,158 | 7/1993 | Jardieu . |
| 5,316,921 | 5/1994 | Godowski et al. |
| 5,328,837 | 7/1994 | Godowski et al. |
| 5,362,716 | * 11/1994 | Kmiecik et al. |
| 5,547,856 | * 8/1996 | Godowski . |
| 5,646,036 | * 7/1997 | Schwall et al. |
| 5,686,292 | * 11/1997 | Schwall et al. |

FOREIGN PATENT DOCUMENTS

| | | |
|---|---|---|
| 0 567 585 | 11/1993 | (EP) . |
| WO 92/05184 | 4/1992 | (WO) . |
| WO 92/13097 | 8/1992 | (WO) . |
| WO 93/20792 | 11/1992 | (WO) . |
| WO 93/15754 | 8/1993 | (WO) . |
| WO 93/23541 | 11/1993 | (WO) . |
| WO 93/23550 | 11/1993 | (WO) . |
| WO 94/04679 | 3/1994 | (WO) . |
| WO 94/06909 | 3/1994 | (WO) . |
| WO 94/29348 | 12/1994 | (WO) . |
| WO 95/01376 | 12/1995 | (WO) . |

OTHER PUBLICATIONS

U.S. application No. 09/669,971, Schwall et al., filed Sep. 2000.*
U.S. application No. 08/952,235, Schwall et al., filed Feb. 1998.*
U.S. application No. 08/459,849, Schwall et al., filed Jun. 1995.*
Comoglio et al, "The HGF Receptor and Its Ligand: Structure, Signal Transduction and Biology", Cell Biology International, vol. 18, p. 375 1994.*
*Handbook of Monoclonal Antibodies*, Ferrone et al. eds., Park Ridge, NJ:Noyes Publications, pp. 302–359 and Chapter 22 (1985).
Asami et al., "Purification and Characterization of Hepatocyte Growth Factor from Injured Liver of Carbon Tetrachloride–Treated Rats" *J. Biochem.* 109:8–13 (1991).
Bellusci et al., "Creation of an Hepatocyte Growth Factor/Scatter Factor Autocrine Loop in Carcinoma Cells Induces Invasive Properties Associated with Increased Tumorigenicity" *Oncogene* 9:1091–1099 (1994).
Boerner et al., "Production of Antigen–Specific Human Monoclonal Antibodies From In Vitro–Primed Human Splenocytes" *The Journal of Immunology* 147(1):86–95 (1991).
Bottaro et al., "Identification of the Hepatocyte Growth Factor Receptor as the c–met Proto–Oncogene Product" *Science* 251:802–804 (Feb. 15, 1991).
Brodeur et al., "Mouse–Human Myeloma Partners for the Production of Heterohybridomas" *Monoclonal Antibody Production Techniques and Applications*, New York:Marcel Dekker, Inc. pp. 51–63 (1987).
Bruggemann et al., "Designer Mice: The Production of Human Antibody Repertoires in Transgenic Animals" *Year in Immunology* 7:33–40 (1993).
Carter et al., "Humanization of an anti–p185$^{HER2}$ antibody for human cancer therapy" *Proc. Natl. Acad. Sci.* 89:4285–4289 (1992).
Chamow et al., "A Humanized, Bispecific Immunoadhesin–Antibody That Retargets CD3$^+$ Effectors to Kill HIV–1–Infected Cells" *Journal of Immunology* 153:4268–4280 (1994).

(List continued on next page.)

Primary Examiner—Nancy A. Johnson
(74) Attorney, Agent, or Firm—Piper Marbury Rudnick & Wolfe LLP; Steven B. Kelber

(57) ABSTRACT

Hepatocyte growth factor (HGF) receptor antagonists are provided. The HGF receptor antagonists include HGF receptor antibodies and fragments thereof. The HGF receptor antagonists can be employed to block binding of HGF to HGF receptors or substantially inhibit HGF receptor activation. The HGF receptor antagonists may be included in pharmaceutical compositions, articles of manufacture, or kits. Methods of treating cancer using the HGF receptor antagonists are also provided.

16 Claims, 3 Drawing Sheets

OTHER PUBLICATIONS

Chan et al., "Identification of a Competetive HGF Antagonist Encoded by an Alternative Transcript" *Science* 254:1382–1385 (1991).

Chan et al., "Isoforms of Human HGF and their Biological Activities" *Hepatocyte Growth Factor–Scatter Factor (HGF–SF) and the C–Met Receptor*, I.D. Goldberg and E.M. Rosen eds., Basel:Birkhauser Verlag pp. 67–79 (1993).

Chothia and Lesk, "Cononical structures for the hypervariable regions of immmunoglobulins" *J. Mol. Biol.* 196(4):901–917 (1987).

Chothia, Cyrus, "Domain Association in Immunoglobulin Molecules: The Packing of Variable Domains" *J. Mol. Biol.* 186:651–663 (1985).

Cole et al., "The EBV–Hybridoma Technique and Its Application to Human Lung Cancer" *Monoclonal Antibodies and Cancer Therapy*, Reisfeld et al., New York:Alan R. Liss, Inc. pp. 77–96 (1985).

Comoglio, "The HGF Receptor and Its Ligand: Structure, Signal Transduction and Biology" *Cell Biology International* (abstract only) 18(5):375 (1994).

Comoglio, "Structure, Biosynthesis and Biochemical Properties of the HGF Receptor in Normal and Malignant Cells" *Hepatocyte Growth Factor–Scatter Factor (HGF–SF) and the C–Met Receptor*, I.D. Goldberg and E.M. Rosen eds., Basel:Birkhauser Verlag pp. 131–165 (1993).

Cooper et al., "Amplification and Overexpression of the MET Gene in Spontaneously Transformed NIH3T3 Mouse Fibroblasts" *EMBO Journal* 5(10):2623–2628 (1986).

Crepaldi et al., "Targeting of the SF/HGF Receptor to the Basolateral Domain of Polarized Epithelial Cells" *The Journal of Cell Biology* 125(2):313–320 (1994).

David et al., "Protein Iodination with Solid State Lactoperoxidase" *Biochemistry* 13(5):1014–1021 (1974).

de Sauvage et al., "Stimulation of Megakaryocytopoiesis and Thrombopoiesis by the c–Mpl Ligand" *Nature* 369:533–538 (Jun. 16, 1994).

Defrances et al., "The Presence of Hepatocyte Growth Factor in the Developing Rat" *Development* 116:387–395 (1992).

De Renzo et al., "Overexpression of the c–MET/HGF Receptor Gene in Human Thyroid Carcinomas" *Oncogene* 7:2549–2553 (1992).

Di Renzo et al., "Selective Expression of the Met/HGF Receptor in Human Central Nervous System Microglia" *Oncogene* 8:219–222 (1993).

Fan et al., "Blockade of Epidermal Growth Factor Receptor Function by Bivalent and Monovalent Fragments of 225 Anti–Epidermal Growth Factor Receptor Monoclonal Antibodies" *Cancer Research* 53:4322–4328 (1993).

Giordano et al., "Transfer of Motogenic and Invasive Response to Scatter Factor/Hepatocyte Growth Factor by Transfection of Human met Protooncogene" *Proc. Natl. Acad. Sci. USA* 90:649–653 (Jan. 1993).

Giordano et al., "Tyrosine Kinase Receptor Indistiguishable from the C–Met Protein" *Nature* 339:155–156 (May 11, 1989).

Goding, "Production of Monoclonal Antibodies" *Monoclonal Antibodies: Principles and Practice*, Academic Press, pp. 59–103 (1986).

Gohda et al., "Purification and Partial Characterization of Hepatocyte Growth Factor from Plasma of a Patient with Fulminant Hepatic Failure" *J. Clin. Invest.* 81:414–419 (1988).

Gorman, C., "High Efficiency Gene Transfer Into Mammalian Cells" *DNA Cloning: A Practical Approach*, Glover, D.M., ed, Washington D.C.:IRL Press vol. 2:143–190 (1985).

Han et al., "Characterization of the DNF15S2 Locus on Human Chromosome 3: Identification of a Gene Coding for Four Kringle Domains with Homology to Hepatocyte Growth Factor" *Biochemistry* 30:9768–9780 (1991).

Harris et al., "Therapeutic Antibodies—The Coming of Age" *Tibtech* 11:42–44 (Feb. 1993).

Hartmann et al., "A Functional Domain in the Heavy Chain of Scatter Factor/Hepatocyte Growth Factor Binds the c–Met Receptor and Induces Cell Dissociation but Not Mitogenesis" *Proc. Natl. Acad. Sci. USA* 89:11574–11578 (Dec. 1992).

Hoogenboom and Winter, "By–passing immunisation: human antibodies from synthetic repertoires of germline $V_H$ gene segments rearranged in vitro" *J. Mol. Biol.* 227:381–388 (1992).

Hunter et al., "Preparation of Iodine 131 Labelled Human Growth Hormone of High Specific Activity" *Nature* 194:495–496 (1962).

Igawa et al., "Hepatocyte Growth Factor is a Potent Mitogen for Cultured Rabbit Renal Tubular Epithelial Cells" *Biochem. & Biophys. Res. Comm.* 174(2):831–838 (Jan. 31, 1991).

Iyer et al., "Structure, Tissue–Specific Expression, and Transforming Activity of the Mouse met Protooncogene" *Cell Growth & Differentiation* pp. 87–95 (1990).

Jakobovits et al., "Analysis of Homozygous Mutant Chimeric Mice: Deletion of the Immunoglobulin Heavy–Chain Joining Region Blocks B–cell Development and Antibody Production" *Proc. Natl. Acad. Sci. USA* 90:2551–2555 (Mar. 1993).

Jakobovits et al., "Germ–line Transmission and Expression of a Human–Derived Yeast Artificial Chromosome" *Nature* 362:255–258 (Mar. 18, 1993).

Jones et al., "Replacing the Complementarity–determined Regions in a Human Antibody with Those From a Mouse" *Nature* 321:522–525 (May 29, 1986).

Kohler et al., "Continuous Cultures of Fused Cells Secreting Antibody of Predefined Specificity" *Nature* 256:495–497 (Aug. 7, 1975).

Kozbor et al., "A Human Hybrid Myeloma for Production of Human Monoclonal Antibodies" *The Journal of Immunology* 133(6):3001–3005 (1984).

Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Administration" *Hepatology* 13(4):743–750 (1991).

Lokker et al., "Generation and Characterization of a Competitive Antagonist of Human Hepatocyte Growth Factor, HGF/NK1" *Journal of Biological Chemistry* 268(23):17145–17150 (Aug. 15, 1993).

Lokker et al., "Structure–Function Analysis of Hepatocyte Growth Factor: Identification of Variants that Lack Mitogenic Activity Yet Retain High Affinity Receptor Binding" *EMBO Journal* 11(7):2503–2510 (1992).

Mark et al., "Expression and Characterization of Hepatocyte Growth Factor Receptor–IgG Fusion Proteins" *The Journal of Biological Chemistry* 267(36):26166–26171 (Dec. 25, 1992).

Marks et al., "By-passing immunization: human antibodies from V-gene libraries displayed on phage" *J. Mol. Biol.* 222:581–597 (1991).

Matsumoto et al., "Deletion of Kringle Domains or the N-Terminal Hairpin Structure in Hepatocyte Growth Factor Results in Marked Decreases in Related Biological Activities" *Biochem. & Biophys. Res. Comm.* 181(2):691–699 (Dec. 16, 1991).

Matsumoto et al., "Hepatocyte Growth Factor is a Potent Stimulator of Human Melanocyte DNA Synthesis and Growth" *Biochem. & Biophys. Res. Comm.* 176(1):45–51 (Apr. 15, 1991).

Michalopoulos et al., "Control of Hepatocyte Replication by Two Serum Factors" *Cancer Research* 44:4414–4419 (Oct. 1984).

Miyazawa et al., "An Alternatively Processed mRNA Generated from Human Hepatocyte Growth Factor Gene" *European Journal of Biochemistry* 197:15–22 (1991).

Miyazawa et al., "Molecular Cloning and Sequence Analysis of cDNA for Human Hepatocyte Growth Factor" *Biochem. & Biophys. Res. Comm.* 163(2):967–973 (Sep. 15, 1989).

Montesano et al., "Identification of a Fibroblast–Derived Epithelial Morphogen as Hepatocyte Growth Factor" *Cell* 67:901–908 (Nov. 29, 1991).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Munson et al., "LIGAND: A Versatile Computerized Approach for Characterization of Ligand–Binding Systems" *Analytical Biochemistry* 107:220–239 (1980).

Naka et al., "Activation of Hepatocyte Growth Factor by Proteolytic Conversion of a Single Chain Form to a Heterodimer" *The Journal of Biological Chemistry* 267(28):20114–20119 (1992).

Nakamura et al., "Molecular Cloning and Expression of Human Hepatocyte Growth Factor" *Nature* 342:440–443 (Nov. 23, 1989).

Nakamura et al., "Partial Purification and Characterization of Hepatocyte Growth Factor from Serum of Hepatectomized Rats" *Biochem. & Biophys. Res. Comm.* 122:1450–1459 (Aug. 16, 1984).

Nakamura et al., "Purification and Characterization of a Growth Factor from Rat Platelets for Mature Parenchymal Hepatocytes in Primary Cultures" *Proc. Natl. Acad. Sci. USA* 83:6489–6493 (1986).

Nakamura et al., "Purification and Subunit Structure of Hepatocyte Growth Factor from Rat Platelets" *FEBS Letters* 224(2):311–316 (Nov. 1987).

Naldini et al., "Hepatocyte Growth Factor (HGF) Stimulates the Tyrosine Kinase Activity of the Receptor Encoded by the Proto–Oncogene c–MET" *Oncogene* 6:501–504 (1991).

Naldini et al., "Scatter Factor and Hepatocyte Growth Factor are Indistinguishable Ligands for the MET Receptor" *EMBO Journal* 10(10):2867–2878 (1991).

Novotny and Haber, "Structural invariants of antigen binding: comparison of immunoglobulin $V_L-V_H$ and $V_L-V_L$ domain dimers" *Proc. Natl. Acad. Sci. USA* 82(14):4592–4596 (Jul. 1985).

Nygren, H., "Conjugation of Horseradish Peroxidase to Fab Fragments with Different Homobifunctional and Heterobifunctional Cross–Linking Reagents" *The Journal of Histochemistry and Cytochemistry* 30(5):407–412 (1982).

Okajima et al., "Primary Structure of Rat Hepatocyte Growth Factor and Induction of Its mRNA During Liver Regeneration Following Hepatic Injury" *European Journal of Biochemistry* 193:375–381 (1990).

Pain et al., "Preparation of Protein A–Peroxidase Monoconjugate Using a Heterobifunctional Reagent, and its Use in Enzyme Immunoassays" *Journal of Immunological Methods* 40:219–230 (1981).

Palacios et al., "IL3–Dependent Mouse Clones That Express B–220 Surface Antigen, Contain Ig Genes in Germ–Line Configuration, and Generate B Lymphocytes In Vivo" *Cell* 41:727–734 (1985).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

Ponzetto et al., "c–met is Amplified But Not Mutated in a Cell Line with an Activated met Tyrosine Kinase" *Oncogene* 6:553–559 (1991).

Ponzetto et al., "A Novel Recognition Motif for Phosphatidylinositol 3–Kinase Binding Mediates Its Association With The Hepatocyte Growth Factor/Scatter Factor Receptor" *Molecular & Cellular Biology* 13(8):4600–4608 (1993).

Prat et al., "C–Terminal Truncated Forms of Met, the Hepatocyte Growth Factor Receptor" *Molecular & Cellular Biology* 11(12):5954–5962 (1991).

Prat et al., "The Receptor Encoded by the Human c–Met Oncogene is Expressed in Hepatocytes, Epithelial Cells and Solid Tumors" *Int. J. Cancer* 49:323–328 (1991).

Presta et al., "Humanization of an Antibody Directed Against IgE" *J. Immunol.* 151(5):2623–2632 (Sep. 1, 1993).

Presta, L., "Antibody Engineering" *Curr. Op. Struct. Biol.* 2:593–596 (1992).

Riechmann et al., "Reshaping Human Antibodies for Therapy" *Nature* 332:323–327 (Mar. 24, 1988).

Rodrigues et al., "Alternative Splicing Generates Isoforms of the met Receptor Tyrosine Kinase Which Undergo Differential Processing" *Molecular & Cellular Biology* 11(6):2962–2970 (1991).

Rubin et al., "A Broad–Spectrum Human Lung Fibroblast–Derived Mitogen is a Variant of Hepatocyte Growth Factor" *Proc. Natl. Acad. Sci. USA* 88:415–419 (1991).

Russell et al., "Partial Characterization of a Hepatocyte Growth Factor From Rat Platelets" *J. Cellular Physiology* 119:183–192 (1984).

Seki et al., "Isolation and Expression of cDNA for Different Forms of Hepatocyte Growth Factor from Human Leukocyte" *Biochem. and Biophys. Res. Commun.* 172(1):321–327 (Oct. 15, 1990).

Sims et al., "A Humanized CD18 Antibody Can Block Function Without Cell Destruction" *The Journal of Immunology* 151(4):2296–2308 (Aug. 1993).

Smith et al., "Cardiac Glycoside–Specific Antibodies in the Treatment of Digitalis Intoxication" *Antibodies in Human Diagnosis and Therapy* pp. 365–389 (1977).

Stoker et al., "Scatter Factor is a Fibroblast–Derived Modulator of Epithelial Cell Mobility" *Nature* 327:239–242 (May 21, 1987).

Sunitha et al., "Hepatocyte Growth Factor Stimulates Invasion Across Reconstituted Basement Membranes by a New Human Small Intestinal Cell Line" *Clin. Exp. Metastasis* 12:143–154 (1994).

Tashiro et al., "Deduced Primary Structure of Rat Hepatocyte Growth Factor and Expression of the mRNA in Rat Tissues" *Proc. Natl. Acad. Sci. USA* 87:3200–3204 (1990).

Verhoeyen et al., "Reshaping Human Antibodies: Grafting an Antilysozyme Activity" *Science* 239:1534–1536 (Mar. 25, 1988).

Weidner et al., "Scatter Factor: Molecular Characteristics and Effect on the Invasiveness of Epithelial Cells" *Journal of Cell Biology* 111:2097–2108 (Nov. 1990).

Yamada et al., "Immunohistochemistry with Antibodies to Hepatocyte Growth Factor and its Receptor Protein (c–MET) in Human Brain Tissues" *Brain Research* 637:308–312 (1994).

Zola, "Using Monoclonal Antibodies: Soluble Antigens" *Monoclonal Antibodies: A Manual of Techniques*, CRC Press, Chapter 6, pp. 147–158 (1987).

\* cited by examiner

HEPATOCYTE GROWTH FACTOR RECEPTOR ANTAGONISTS AND USES THEREOF

This is a continuation of application Ser. No. 08/459,849 filed on Jun. 2, 1995, now abandoned, which application is incorporated herein by reference and to which application(s) priority is claimed under 35 USC §120.

FIELD OF THE INVENTION

This application relates to hepatocyte growth factor receptor antagonists. The application also relates to the use of the antagonists in therapy or diagnosis of particular pathological conditions in mammals, including cancer.

BACKGROUND OF THE INVENTION

Hepatocyte growth factor ("HGF") functions as a growth factor for particular tissues and cell types. HGF was identified initially as a mitogen for hepatocytes [Michalopoulos et al., Cancer Res., 44:4414–4419 (1984); Russel et al., J. Cell. Physiol., 119:183–192 (1984); Nakamura et al., Biochem. Biophys. Res. Comm., 122:1450–1459 (1984)]. Nakamura et al., supra, reported the purification of HGF from the serum of partially hepatectomized rats. Subsequently, HGF was purified from rat platelets, and its subunit structure was determined [Nakamura et al., Proc. Natl. Acad. Sci. USA, 83:6489–6493 (1986); Nakamura et al., FEBS Letters, 224:311–316 (1987)]. The purification of human HGF ("huHGF") from human plasma was first described by Gohda et al., J. Clin. Invest., 81:414–419 (1988).

Both rat HGF and huHGF have been molecularly cloned, including the cloning and sequencing of a naturally occurring variant lacking 5 amino acids designated "delta5 HGF" [Miyazawa et al., Biochem. Biophys. Res. Comm., 163:967–973 (1989); Nakamura et al., Nature, 342:440–443 (1989); Seki et al., Biochem. Biophys. Res. Commun., 172:321–327 (1990); Tashiro et al., Proc. Natl. Acad. Sci. USA, 87:3200–3204 (1990); Okajima et al., Eur. J. Biochem., 193:375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the huHGF cDNA reveals that both the α- and the β-chains are contained in a single open reading frame coding for a pre-pro precursor protein. In the predicted primary structure of mature huHGF, an interchain S—S bridge is formed between Cys 487 of the α-chain and Cys 604 in the β-chain [see Nakamura et al., Nature, supra]. The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four kringle domains. The kringle 1 domain extends from about aa 128 to about aa 206, the kringle 2 domain is between about aa 211 and about aa 288, the kringle 3 domain is defined as extending from about aa 303 to about aa 383, and the kringle 4 domain extends from about aa 391 to about aa 464 of the α-chain.

The definition of the various kringle domains is based on their homology with kringle-like domains of other proteins (such as prothrombin and plasminogen), therefore, the above limits are only approximate. To date, the function of these kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, huHGF appears to have no proteolytic activity, and the precise role of the β-chain remains unknown. HGF contains four putative glycosylation sites, which are located at positions 294 and 402 of the α-chain and at positions 566 and 653 of the β-chain.

In a portion of cDNA isolated from human leukocytes, in-frame deletion of 15 base pairs was observed. Transient expression of the cDNA sequence in COS-1 cells revealed that the encoded HGF molecule (delta5 HGF) lacking 5 amino acids in the kringle 1 domain was fully functional [Seki et al., supra].

A naturally occurring huHGF variant has been identified which corresponds to an alternative spliced form of the huHGF transcript containing the coding sequences for the N-terminal finger and first two kringle domains of mature huHGF [Chan et al., Science, 254:1382–1385 (1991); Miyazawa et al., Eur. J. Biochem., 197:15–22 (1991)]. This variant, designated HGF/NK2, has been proposed to be a competitive antagonist of mature huHGF. Comparisons of the amino acid sequence of rat HGF with that of huHGF have revealed that the two sequences are highly conserved and have the same characteristic structural features. The length of the four kringle domains in rat HGF is exactly the same as in huHGF. Furthermore, the cysteine residues are located in exactly the same positions, an indication of similar three-dimensional structures [Okajima et al., supra; Tashiro et al., supra].

HGF and HGF variants are described further in U.S. Pat. Nos. 5,227,158, 5,316,921, and 5,328,837.

The HGF receptor has been identified as the product of the c-Met proto-oncogene [Bottaro et al., Science, 251:802–804 (1991); Naldini et al., Oncogene, 6:501–504 (1991); WO 92/13097 published Aug. 6, 1992; WO 93/15754 published Aug. 19, 1993]. The receptor is usually referred to as "c-Met" or "p190$^{MET}$" and typically comprises, in its native form, a 190-kDa heterodimeric (a disulfide-linked 50-kDa α-chain and a 145-kDa β-chain) membrane-spanning tyrosine kinase protein [Park et al., Proc. Natl. Acad. Sci. USA, 84:6379–6383 (1987)]. Several truncated forms of the c-Met receptor have also been described [WO 92/20792; Prat et al., Mol. Cell. Biol., 11:5954–5962 (1991)].

The binding activity of HGF to its receptor is believed to be conveyed by a functional domain located in the N-terminal portion of the HGF molecule, including the first two kringles [Matsumoto et al., Biochem. Biophys. Res. Commun., 181:691–699 (1991); Hartmann et al., Proc. Natl. Acad. Sci., 89:11574–11578 (1992); Lokker et al., EMBO J., 11:2503–2510 (1992); Lokker and Godowski, J. Biol. Chem., 268:17145–117150 (1991)]. The c-Met protein becomes phosphorylated on tyrosine residues of the 145-kDa β-subunit upon HGF binding.

Certain antibodies to HGF receptor have been reported in the literature. Several such antibodies are described below.

Prat et al., Mol. Cell. Biol., supra, describe several is monoclonal antibodies specific for the extracellular domain of the β-chain encoded by the c-Met gene [see also, WO 92/20792]. The monoclonal antibodies were selected following immunization of Balb/c mice with whole living GTL-16 cells (human gastric carcinoma cell line) overexpressing the Met protein. The spleen cells obtained from the immunized mice were fused with Ag8.653 myeloma cells, and hybrid supernatants were screened for binding to GTL-16 cells. Four monoclonal antibodies, referred to as DL-21, DN-30, DN-31 and DO-24, were selected.

Prat et al., *Int. J. Cancer*, 49:323–328 (1991) describe using anti-c-Met monoclonal antibody DO-24 for detecting distribution of the c-Met protein in human normal and neoplastic tissues [see, also, Yamada et al., *Brain Research*, 637:308–312 (1994)]. The murine monoclonal antibody DO-24 was reported to be an IgG2a isotype antibody.

Crepaldi et al., *J. Cell Biol.*, 125: 313–320 (1994) report using monoclonal antibodies DO-24 and DN-30 [described in Prat et al., *Mol. Cell. Biol.*, supra] and monoclonal antibody DQ-13 to identify subcellular distribution of HGF receptors in epithelial tissues and in MDCK cell monolayers. According to Crepaldi et al., monoclonal antibody DQ-13 was raised against a peptide corresponding to nineteen COOH-terminal amino acids (from $Ser^{1372}$ to $Ser^{1390}$) of the human c-Met sequence.

A monoclonal antibody specific for the cytoplasmic domain of human c-Met has also been described [Bottaro et al., supra].

Several of the monoclonal antibodies referenced above are commercially available from Upstate Biotechnology Incorporated, Lake Placid, N.Y. Monoclonal antibodies DO-24 and DL-21, specific for the extracellular epitope of c-Met, are available from Upstate Biotechnology Incorporated. Monoclonal antibody DQ-13, specific for the intracellular epitope of c-Met, is also available from Upstate Biotechnology Incorporated.

Various biological activities have been described for HGF and its receptor [see, generally, Chan et al., *Hepatocyte Growth Factor-Scatter Factor (HGF-SF) and the C-Met Receptor*, Goldberg and Rosen, eds., Birkhauser Verlag-Basel (1993), pp. 67–79]. It has been observed that levels of HGF increase in the plasma of patients with hepatic failure [Gohda et al., supra] and in the plasma [Lindroos et al., *Hepatol.*, 13:734–750 (1991)] or serum [Asami et al., *J. Biochem.*, 109:8–13 (1991)] of animals with experimentally induced liver damage. The kinetics of this response are usually rapid, and precedes the first round of DNA synthesis during liver regeneration. HGF has also been shown to be a mitogen for certain cell types, including melanocytes, renal tubular cells, keratinocytes, certain endothelial cells and cells of epithelial origin [Matsumoto et al., *Biochem. Biophys. Res. Commun.*, 176:45–51 (1991); Igawa et al., *Biochem. Biophys. Res. Commun.*, 174:831–838 (1991); Han et al., *Biochem.*, 30:9768–9780 (1991); Rubin et al., *Proc. Natl. Acad. Sci. USA*, 88:415–419 (1991)]. Both HGF and the c-Met protooncogene have been postulated to play a role in microglial reactions to CNS injuries [DiRenzo et al., *Oncogene*, 8:219–222 (1993)].

HGF can also act as a "scatter factor", an activity that promotes the dissociation of epithelial and vascular endothelial cells in vitro [Stoker et al., *Nature*, 327:239–242 (1987); Weidner et al., *J. Cell Biol.*, 111:2097–2108 (1990); Naldini et al., *EMBO J.*, 10:2867–2878 (1991); Giordano et al., *Proc. Natl. Acad. Sci. USA*, 90:649–653 (1993)]. Moreover, HGF has recently been described as an epithelial morphogen [Montesano et al., *Cell*, 67:901–908 (1991)]. Therefore, HGF has been postulated to be important in tumor invasion [Comoglio, *Hepatocyte Growth Factor-Scatter Factor (HGF-SF) and the C-Met Receptor*, Goldberg and Rosen, eds., Birkhauser Verlag-Basel (1993), pp. 131–165]. Bellusci et al., *Oncogene*, 9:1091–1099 (1994) report that HGF can promote motility and invasive properties of NBT-II bladder carcinoma cells.

c-Met RNA has been detected in several murine myeloid progenitor tumor cell lines [Iyer et al., *Cell Growth and Differentiation*, 1:87–95 (1990)]. Further, c-Met is expressed in various human solid tumors [Prat et al., *Int. J. Cancer*, supra] Overexpression of the c-Met oncogene has also been suggested to play a role in the pathogenesis and progression of thyroid tumors derived from follicular epithelium [DiRenzo et al., *Oncogene*, 7:2549–2553 (1992)]. Chronic c-Met/HGF receptor activation has also been observed in certain malignancies [Cooper et al., *EMBO J.*, 5:2623 (1986); Giordano et al., *Nature*, 339:155 (1989)].

In view of the role of HGF and/or c-Met in potentiating or promoting such diseases or pathological conditions, it would be useful to have a means of substantially reducing or inhibiting one or more of the biological effects of HGF and its receptor.

SUMMARY OF THE INVENTION

The invention provides HGF receptor antagonists which are capable of specifically binding to a HGF receptor. Preferred HGF receptor antagonists are capable of substantially reducing or inhibiting the mitogenic, motogenic or other biological activity of HGF or HGF receptor activation, and thus are useful in the treatment of various diseases and pathological conditions such as cancer. In one embodiment of the invention, the HGF receptor antagonist is an antibody. Preferably, the antagonist is a monoclonal antibody, and more preferably, is a Fab fragment of a monoclonal antibody.

The invention also provides hybridoma cell lines which produce HGF receptor antagonistic monoclonal antibodies, and isolated nucleic acid encoding HGF receptor antagonistic is antibodies.

The invention also provides pharmaceutical compositions comprising one or more HGF receptor antagonists in a pharmaceutically-acceptable carrier. In one embodiment, the pharmaceutical composition may be included in an article of manufacture or kit.

The invention further provides methods for treating cancer comprising administering to a mammal diagnosed as having cancer an effective amount of a HGF receptor antagonist. The HGF receptor antagonist alone may be administered to the mammal, or alternatively, may be administered to the mammal in combination with other therapeutic agents such as anti-cancer agents.

It is believed that the antagonists can be used to block binding of HGF to HGF receptor(s) or substantially prevent receptor activation, thereby treating pathologic conditions associated with binding of HGF to HGF receptor(s) or with the activation of HGF receptor(s).

DETAILED DESCRIPTION OF THE INVENTION

I. Definitions

Figure 1:
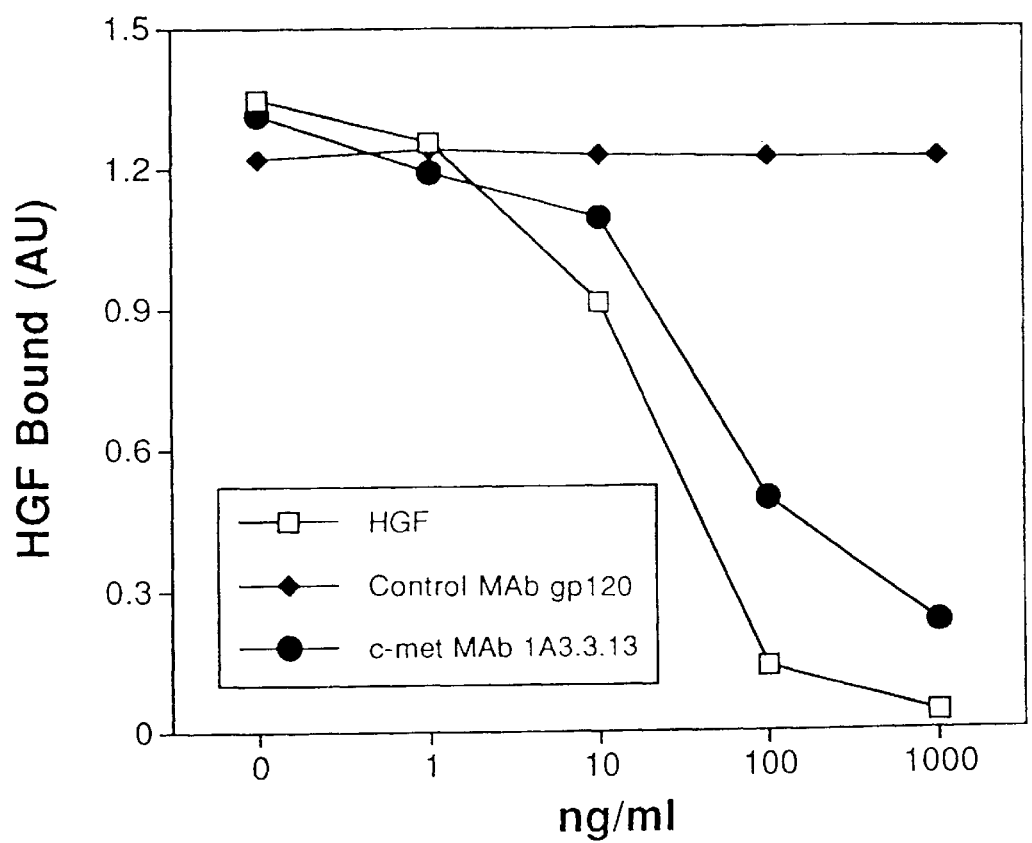
FIG. 1 is a graph showing the inhibition of HGF binding to c-Met-IgG fusion protein by monoclonal antibody 1A3.3.13.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al., 1989, supra, or Nakamura et al., 1989, supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as $p190^{MET}$. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., *Mol. Cell. Biol.*, 11:2962–2970 (1991); Park et al., *Proc. Natl. Acad. Sci.*, 84:6379–6383 (1987); or Ponzetto et al., *Oncogene*, 6:553–559 (1991).

The terms "agonist" and "agonistic" when used herein refer to or describe a molecule which is capable of, directly or indirectly, substantially inducing, promoting or enhancing HGF biological activity or HGF receptor activation.

The terms "antagonist" and "antagonistic" when used herein refer to or describe a molecule which is capable of, directly or indirectly, substantially counteracting, reducing or inhibiting HGF biological activity or HGF receptor activation.

The term "HGF biological activity" when used herein refers to any mitogenic, motogenic or morphogenic activities of HGF or any activities occurring as a result of HGF binding to a HGF receptor. The term "HGF receptor activation" refers to HGF receptor dimerization or HGF receptor-induced tyrosine kinase activity. HGF receptor activation may occur as a result of HGF binding to a HGF receptor, but may alternatively occur independent of any HGF binding to a HGF receptor. HGF biological activity may, for example, be determined in an in vitro or in vivo assay of hepatocyte growth promotion. Adult rat hepatocytes in primary culture have been used to test the effect of HGF on hepatocyte proliferation. Accordingly, the effect of a HGF receptor antagonist can be determined in an assay suitable for testing the ability of HGF to induce DNA synthesis of rat hepatocytes in primary cultures. Human hepatocytes can be cultured similarly to the methods established for preparing primary cultures of normal rat hepatocytes. Alternatively, the effect of a HGF receptor antagonist can be determined in an assay suitable for testing the ability of HGF to induce DNA synthesis in other types of cells expressing HGF receptor(s), such as mink lung cells or human mammary epithelial cells described in Examples 3 and 4. DNA synthesis can, for example, be assayed by measuring incorporation of $^3$H-thymidine into DNA. The effectiveness of the HGF receptor antagonist can be determined by its ability to block proliferation and incorporation of the $^3$H-thymidine into DNA. The effect of HGF receptor antagonists can also be tested in vivo in animal models.

The term "antibody" is used herein in a broad sense and includes intact immunoglobulin molecules and immunoglobulin fragments (such as Fab, F(ab')$_2$, or Fv), so long as they exhibit any of the desired antagonistic properties described herein. Antibodies are typically proteins which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Clothia et al., *J. Mol. Biol.*, 186:651–663 (1985); Novotny and Haber, *Proc. Natl. Acad. Sci. USA*, 82:4592–4596 (1985)]. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunological Interest*, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity [U.S. Pat. No. 4,816,567; Morrison et al., *Proc. Natl. Acad. Sci. USA*, 81:6851–6855 (1984)].

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

II. Compositions and Methods of the Invention

In one embodiment of the invention, HGF receptor antagonists are provided. Non-limiting examples of HGF receptor antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. The HGF receptor antagonists of the invention are preferably HGF receptor antibodies. For instance, the antagonistic antibodies may be polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Preferably, the immunizing agent includes the c-Met polypeptide or a fusion protein thereof. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for HGF receptor antibody titer. If desired, the mammal can be boosted until the antibody titer increases or plateaus.

The antagonistic antibodies of the invention may, alternatively, be monoclonal antibodies. Antagonistic monoclonal antibodies of the invention may be prepared using hybridoma methods, such as those described by Kohler and Milstein, *Nature*, 256:495 (1975). In a hybridoma method, a mouse or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

Preferably, the immunizing agent includes the c-Met polypeptide or a fusion protein thereof. The immunizing agent may alternatively comprise a fragment or portion of HGF or a HGF receptor having one or more amino acid residues that participate in the binding of HGF to its receptor. In a more preferred embodiment, the immunizing agent comprises an extracellular domain of c-Met fused to an IgG sequence, such as described in Example 1.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. An example of such a murine myeloma cell line is P3X63AgU.1, described in Example 1 below. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against a HGF receptor. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below. The binding affinity of the monoclonal antibody can, for example, be determined by the Scatchard analysis of Munson and Pollard, *Anal. Biochem.*, 107:220 11980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody comprising one antigen-combining site having specificity for a HGF receptor and another antigen-combining site having specificity for a different antigen, such as HER2 or CD3.

It is believed, however, that monovalent antibodies capable of binding to a HGF receptor will be especially useful as HGF receptor antagonists. While not being bound to any particular theory, it is presently believed that activation of c-Met may proceed by a mechanism wherein huHGF binding to c-Met induces aggregation or dimerization of the receptors which in turn activates intracellular receptor kinase activity. Because monovalent antibodies will likely be unable to induce such aggregation or dimerization, the monovalent antibodies should not activate c-Met. Such monovalent antibodies may be directed against the HGF binding site of the receptor or may otherwise be capable of interfering with HGF, its fragments or its variants binding to the HGF receptor, such as by sterically hindering HGF, its fragments or its variants access to the receptor. Alternatively, the monovalent antibodies may be capable of sterically preventing HGF receptor dimerization.

Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion is also described in Example 6 below. Papain digestion of antibodies typically produces two identical antigen binding fragments, called Fab fragments, each with a single antigen binding site, and a residual Fc fragment. Pepsin treatment yields an F(ab')$_2$ fragment that has two antigen combining sites and is still capable of cross-linking antigen.

The Fab fragments produced in the antibody digestion also contain the constant domains of the light chain and the first constant domain (CH$_1$) of the heavy chain. Fab' fragments differ from Fab fragments by the addition of a few residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

In a preferred embodiment of the invention, the antagonists comprise Fab fragments of monoclonal antibodies specific for c-Met. In a more preferred embodiment, the monoclonal antibody Fab fragments have the same biological characteristics as the monoclonal antibody Fab fragments produced by digesting either of the monoclonal antibodies secreted by the hybridoma cell lines deposited under American Type Culture Collection Accession Nos, ATCC HB-11894 or ATCC HB-11895. The term "biological characteristics" is used to refer to the in vitro and/or in vivo activities of the monoclonal antibody, e.g., ability to substantially reduce or inhibit binding of huHGF to c-Met or to substantially reduce or inhibit c-Met activation. Accordingly, the monovalent antibody preferably binds to substantially the same epitope as the 1A3.3.13 antibody or the 5D5.11.6 antibody disclosed herein. This can be determined by conducting assays described herein and in the Examples. For instance, to determine whether a monoclonal antibody has the same specificity as the 1A3.3.13 antibody specifically disclosed (i.e., the antibody having the ATCC deposit No. HB-11894) or the 5D5.11.6 antibody specifically disclosed (i.e., the antibody having the ATCC deposit No. HB-11895), one can use a competitive ELISA binding assay. In a preferred embodiment of the invention, the monoclonal antibody or fragment thereof will inhibit the binding of HGF, its fragments or its variants, or the mitogenic activity of HGF, its fragments, or its variants at least about 50%, preferably, greater than about 80%, and more preferably, greater than about 90%, as determined by an in vitro competitive binding assay or proliferation assay, such as described in the Examples below.

In addition to the antagonistic antibodies described above, it is contemplated that chimeric or hybrid antagonistic antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

The antagonistic antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Reichmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al., *J. Immunol.*, 151:2296 (1993); Chothia and Lesk, *J. Mol. Biol.*, 196:901 (1987)]. Another method uses a particular framework derived from the consensus sequence of all human antibodies of a particular subgroup of light or heavy chains. The same framework may be used for several different humanized antibodies [Carter et al., *Proc. Natl. Acad. Sci. USA*, 89:4285 (1992); Presta et al., *J. Immunol.*, 151:2623 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published Mar. 3, 1994].

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge [see, e.g., Jakobovits et al., *Proc. Natl. Acad. Sci. USA*, 90:2551–255 (1993); Jakobovits et al., *Nature*, 362:255–258 (1993); Bruggermann et al., *Year in Immuno.*, 7:33 (1993)]. Human antibodies can also be produced in phage display libraries [Hoogenboom and Winter, *J. Mol. Biol.*, 227:381 (1991); Marks et al., *J. Mol. Biol.*, 222:581 (1991)]. The techniques of Cote et al. and Boerner et al. are also available for the preparation of human monoclonal antibodies (Cote et al., *Monoclonal Antibodies and Cancer Therapy*, Alan R. Liss, p. 77 (1985) and Boerner et al., *J. Immunol.*, 147(1):86–95 (1991)].

In another embodiment of the invention, methods for treating cancer are provided. In the methods, HGF receptor antagonist is administered to a mammal diagnosed as having cancer. While the term "cancer" as used herein is not limited to any one specific form of the disease, it is believed that the methods will be particularly effective for cancers which are found to be accompanied by increased levels of HGF or expression of c-Met in the mammal. In a preferred method of the invention, the cancer is breast cancer. It is of course contemplated that the methods of the invention can be employed in combination with still other therapeutic techniques such as surgery.

The antagonist is preferably administered to the mammal in a pharmaceutically-acceptable carrier. Suitable carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antagonist, which matrices are in the form of shaped articles, e.g., films, liposomes or microparticles. It will be apparent to those persons skilled in the art that certain carriers may be more preferable depending upon, for instance, the route of administration and concentration of antagonist being administered.

The antagonist can be administered to the mammal by injection (e.g., intravenous, intraperitoneal, subcutaneous, intramuscular), or by other methods such as infusion that ensure its delivery to the bloodstream in an effective form. The antagonist may also be administered by intratumoral, peritumoral, intralesional, or perilesional routes, to exert local as well as systemic therapeutic effects. Local or intravenous injection is preferred.

Effective dosages and schedules for administering the antagonist may be determined empirically, and making such determinations is within the skill in the art. Those skilled in the art will understand that the dosage of antagonist that must be administered will vary depending on, for example, the mammal which will receive the antagonist, the route of administration, the particular type of antagonist used and other drugs being administered to the mammal. Guidance in selecting appropriate doses for antibody antagonists is found in the literature on therapeutic uses of antibodies, e.g., *Handbook of Monoclonal Antibodies*, Ferrone et al., eds., Noges Publications, Park Ridge, N.J., (1985) ch. 22 and pp. 303–357; Smith et al., *Antibodies in Human Diagnosis and Therapy*, Haber et al., eds., Raven Press, New York (1977) pp. 365–389. A typical daily dosage of the antagonist used alone might range from about 1 µg/kg to up to 100 mg/kg of body weight or more per day, depending on the factors mentioned above.

The antagonist may also be administered to the mammal in combination with effective amounts of one or more other therapeutic agents or in conjunction with radiation treatment. Therapeutic agents contemplated include chemotherapeutics as well as immunoadjuvants and cytokines. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. The antagonist may be administered sequentially or concurrently with the one or more other therapeutic agents. The amounts of antagonist and therapeutic agent depend, for example, on what type of drugs are used, the cancer being treated, and the scheduling and routes of administration but would generally be less than if each were used individually.

Following administration of antagonist to the mammal, the mammal's cancer and physiological condition can be monitored in various ways well known to the skilled practitioner. For instance, tumor mass may be observed physically or by standard x-ray imaging techniques.

In another embodiment of the invention, methods for employing the antagonists in vitro in diagnostic assays are provided. For instance, the antagonists may be employed in diagnostic assays to detect overexpression of HGF receptor in specific cells and tissues. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antagonists used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antagonist to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Additionally, antagonistic antibodies of the invention can be used to immunopurify HGF receptor(s).

In a further embodiment of the invention, there are provided articles of manufacture and kits containing materials useful for treating cancer or detecting or purifying HGF receptor.

The article of manufacture comprises a container with a label. Suitable containers include, for example, bottles, vials, and test tubes. The containers may be formed from a variety of materials such as glass or plastic. The container holds a composition which is effective for treating cancer or for detecting or purifying HGF receptor. The active agent in the composition is a HGF receptor antagonist and preferably, comprises Fab fragments of monoclonal antibodies specific for c-Met. The label on the container indicates that the composition is used for treating cancer or detecting or purifying HGF receptor, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All reference citations herein are incorporated by reference.

EXAMPLE 1

Balb/c mice (obtained from Charles River Laboratories) were immunized by injecting 2.5 µg/50 µl c-Met-IgG fusion protein (diluted in MPL-TDM adjuvant purchased from Ribi Immunochemical Research Inc., Hamilton, Mont.) five times into each hind foot pad. Injections were administered on Day 0 and Days 56, 63, 66 and 73. The c-Met-IgG fusion protein (including the extracellular domain of c-Met fused to a human IgG1 heavy chain) was constructed essentially as described by Mark et al., *J. Biol. Chem.*, 267:26166–26171 (1992) and produced in Chinese hamster ovary (CHO) cells. The c-Met-IgG was subsequently purified in a single step using affinity chromatography on immobilized Protein A (Bioprocessing, Inc., Princeton, N.J.), using an elution scheme modified from Chamow et al., *J. Immunol.*, 153:4268–4280 (1994). Culture supernatant was loaded onto a Protein A column equilibrated in 20 mM Tris, pH 7.4, 0.15 M NaCl. The column was washed, first with equilibration buffer, then with equilibration buffer containing 0.5 M tetramethylammonium chloride, to remove non-specifically bound protein. c-Met-IgG was eluted with 20 mM Tris, pH 7.4, 3.5 M MgCl$_2$. This c-Met-IgG eluate was concentrated and exchanged into 20 mM Tris, pH 7.4, 0.15 M NaCl by gel filtration on Sephadex G25 to a final concentration of about 2–4 mg/ml.

On Day 77, popliteal lymph nodes were removed from the mice and a single cell suspension was prepared in DMEM media (obtained from Biowhitakker Corp.) supplemented with 1% penicillin-streptomycin. The lymph node cells were then fused with murine myeloma cells P3X63AgU.1 (ATCC CRL 1597) using 35% polyethylene glycol and cultured in 96-well culture plates. Hybridomas resulting from the fusion were selected in HAT medium. Ten days after the fusion, hybridoma culture supernatants were screened in an ELISA to test for the presence of monoclonal antibodies binding to the c-Met-IgG fusion protein.

In the ELISA, 96-well microtiter plates were coated by adding 50 μl of 2 μg/ml goat anti-human IgG Fc (purchased from Cappel Laboratories) to each well and incubating at 4° C. overnight. The plates were then washed three times with distilled water. The wells in the microtiter plates were blocked with 200 μl of 2% bovine serum albumin and incubated at room temperature for 1 hour. The plates were then washed again three times with distilled water.

After the washing step, 100 μl of 0.4 μg/ml c-Met-IgG fusion protein (as described above) was added to each well. The plates were incubated for 1 hour at room temperature on a shaker apparatus, followed by washing three times with distilled water.

Then, 100 μl of the hybridoma supernatants was added to designated wells. 100 μl of P3X63AgU.1 myeloma cell conditioned medium was added to other designated wells as controls. The plates were incubated at room temperature for 1 hour on a shaker apparatus and then washed three times with distilled water.

Next, 50 μl HRP-conjugated goat anti-mouse IgG Fc (purchased from Cappel Laboratories), diluted 1:1000 in assay buffer (0.5% bovine serum albumin, 0.05% Tween-20, 0.01% Thimersol in PBS), was added to each well and the plates incubated for 1 hour at room temperature on a shaker apparatus. The plates were washed three times with distilled water, followed by addition of 50 μl of substrate (5 mg OPD, 12.5 ml PBS, 5 μl H$_2$)$_2$O) to each well and incubation at room temperature for 10 minutes. The reaction was stopped by adding 50 μl of 2 N H$_2$SO$_4$ to each well, and absorbance at 490 nm was read in an automated microtiter plate reader.

Of 912 hybridoma supernatants screened in the ELISA, 24 supernatants tested positive (calculated as approximately 2 times above background). The supernatants testing positive in the ELISA were further analyzed by FACS analysis using A549 cells (human epidermoid cell line expressing c-Met; ATCC CCL 185) and fluorescein-conjugated mouse anti-IgG. The FACS analysis showed 19/24 supernatants were positive for anti-c-Met antibodies.

EXAMPLE 2

Balb/c mice were immunized as described in Example 1 except that the c-Met-IgG fusion protein injections were administered on Day 0 and Days 7, 14, 21, 28, 211, 273 and 279. On Day 282, lymph nodes were removed and a fusion was conducted as described in Example 1. Hybridoma supernatants were tested according to the ELISA described in Example 1. One of the positive anti-c-Met monoclonal antibodies was called 5D5.11.6. Further antibody analysis showed that the 5D5.11.6 monoclonal antibody is an IgG1 isotype antibody comprising a kappa light chain.

EXAMPLE 3

An inhibition assay was conducted to examine the ability of the antibodies (described in Example 1) to block binding of HGF to c-Met-IgG fusion protein. Prior to conducting the inhibition assay, the 24 hybridoma supernatants determined positive in the ELISA in Example 1 were purified on Protein A-Sepharose columns to yield antibody preparations of about 1 μg/ml.

For the assay, 96-well microtiter plates were coated by adding 100 μl of 2 μg/ml goat anti-human Fc (purchased from Cappel Laboratories) to each well and incubating overnight at 4° C. The plates were then washed with a washing buffer (0.05% Tween-20, 0.01% Thimersol in PBS). Nonspecific binding in the wells was blocked by adding 150 μl blocking buffer (0.5% BSA, 0.01% Thimersol in PBS, pH 7.4) to each well and incubating at room temperature for 2 hours with rapid agitation on an orbital shaker.

Next, continuing at room temperature and agitation on the orbital shaker, the blocking buffer was removed from the wells, and the plates were washed with washing buffer. Next, 100 μl of 10 ng/ml c-Met-IgG fusion protein (described in Example 1) was added to the wells. The plates were incubated for 2 hours and then washed 3 times with washing buffer.

Recombinant human HGF (rhuHGF) was produced in CHO cells using a procedure modified from Naka et al., *J. Biol. Chem.*, 267:20114–20119 (1992). rhuHGF-transfected cells were grown in a 400 L bioreactor in medium containing 20% fetal bovine serum for 8 days. Culture supernatant containing rhuHGF was concentrated and clarified, then conditioned by the addition of solid NaCl to 0.3 M. rhuHGF was then purified in a single step using cation exchange chromatography. Conditioned, concentrated culture supernatant was loaded onto a column of S-Sepharose Fast Flow equilibrated in 20 mM Tris, pH 7.5, 0.3 M NaCl. After washing out unbound protein, rhuHGF was eluted in a linear gradient from 20 mM Tris, pH 7.5, 0.3 M NaCl to 20 mM Tris, pH 7.5, 1.2 M NaCl. rhuHGF-containing fractions were pooled based on SDS-PAGE analysis. The S Sepharose Fast Flow pool was concentrated and exchanged into 20 mM Tris, pH 7.5, 0.5 M NaCl by gel filtration on Sephadex G25 to a final concentration of about 3–5 mg/ml. A rhuHGF stock solution was then prepared by diluting the rhuHGF in assay buffer (0.5% bovine serum albumin, 0.05% Tween-20, 0.01% Thimersol in PBS) to a concentration of 10 μg/ml. A stock solution of control gp120 antibody (Genentech, Inc.) was also prepared by diluting the antibody in assay buffer to a concentration of 10 μg/ml.

Then, 50 μl of either rhuHGF, gp120 antibody or one of the 24 monoclonal antibodies was added to designated wells to yield a final concentration of 1000, 100, 10, or 1 ng/ml/ well. Immediately, 50 μl of 200 ng/ml biotinylated rhuHGF (rhuHGF biotinylated using Biotin-X-NHS obtained from Research Organics, Inc.) was also added to each well. After 2 hours incubation, the wells were washed 3 times with washing buffer. 100 μl HRP-streptavidin (1:2000 dilution in assay buffer) (purchased from Zymed Laboratories), was added to the wells and the plates were incubated for 30 minutes. The plates were washed again 3 times with washing buffer. 50 μl of substrate (5 mg OPD, 12.5 ml PBS, 5 μl $H_2O_2$) was added to the wells and color was allowed to develop for 20 minutes. The reaction was stopped by adding 100 μl 4.5 N sulfuric acid to each well. Absorbance at 492 nm was quantitated in an automated microtiter plate reader.

One of the monoclonal antibodies, referred to as 1A3.3.13, significantly blocked binding of HGF (FIG. 1). Further antibody analysis showed that the 1A3.3.13 monoclonal antibody is an IgG1 isotype antibody comprising a kappa light chain.

EXAMPLE 4

Several different antibodies produced in the fusion described in Example 1, referred to as 3D6, 6G1, and 1A3.3.13, and purified as described in Example 3, were tested and compared for their ability to induce DNA synthesis in a human mammary epithelial cell bioassay.

Human mammary epithelial cells (obtained from Clonetics Corp., No. CC-2551) were passaged in Mammary Epithelial Cell Basal Medium (Clonetics Corp., No. CC-3151). Prior to conducting the bioassay, the cells were trypsinized, washed, and resuspended in assay medium (Basal Medium supplemented with 1 mg/ml BSA, penicillin, streptomycin and L-glutamine) to a concentration of $1 \times 10^5$ cells/ml. Next, 100 μl of the cells were added to the wells of 96-well culture plates. rhuHGF (described in Example 3) was diluted in assay medium at concentrations of 20 ng/ml and 200 ng/ml. The 3D6, 6G1, 1A3.3.13, and control gp 120 antibodies were diluted in assay medium at concentrations of 200 ng/ml and 2 μg/ml. 100 μl of the rhuHGF and antibody preparations was then added to designated wells. The plates were incubated at 37° C. in 5% $CO_2$ for 16 hours.

Next, 1 μCi $^3$H-thymidine was added to each well, and the plates were incubated for 24 hours at 37° and 5% $CO_2$. The human mammary epithelial cells were harvested and the amount of radioactivity incorporated into the DNA was then quantitated in a microplate scintillation counter.

Figure 2:
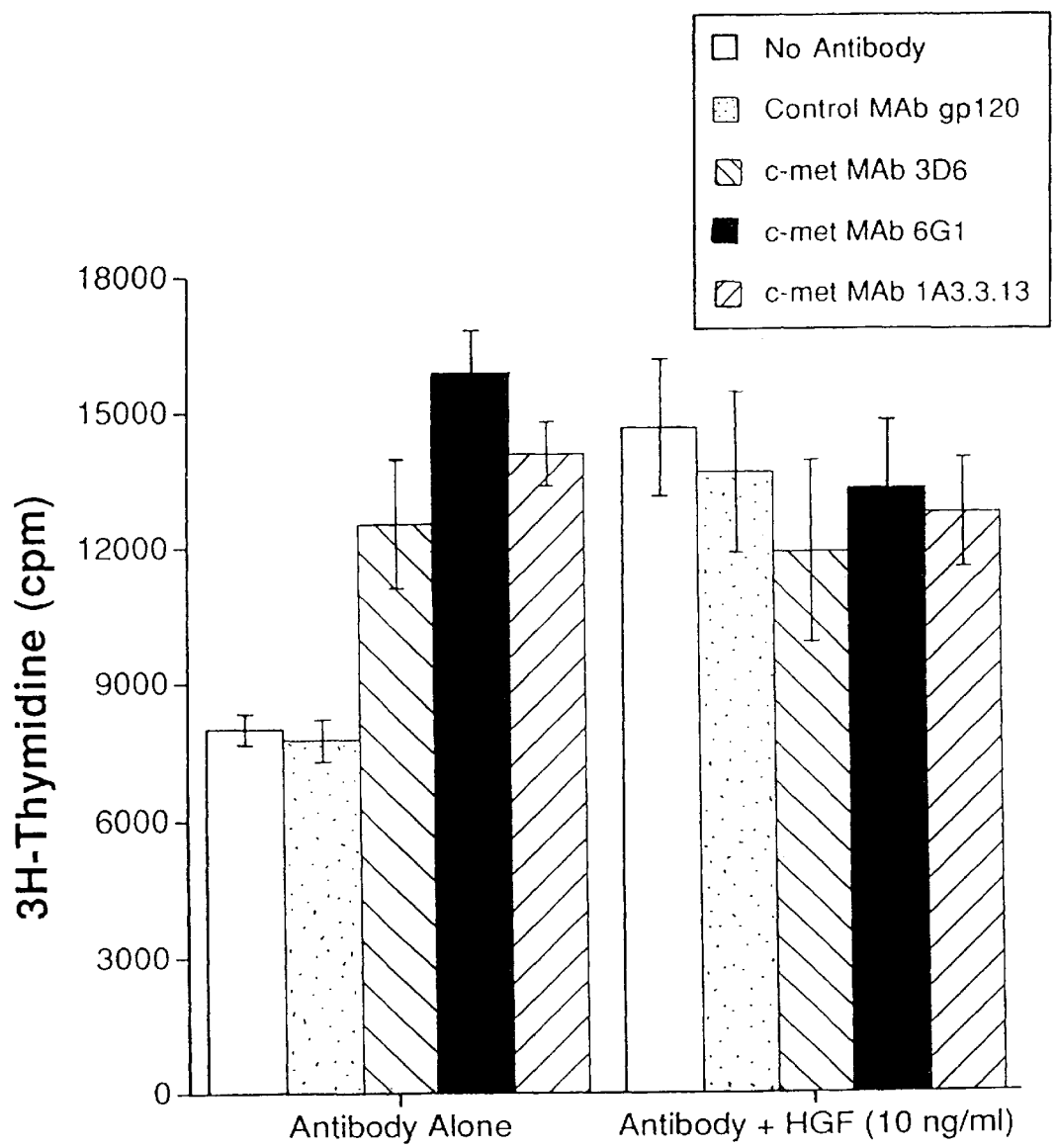
FIG. 2 is a bar diagram showing the stimulatory effect of monoclonal antibodies 3D6, 6G1, and 1A3.3.13 on human mammary epithelial cells in a proliferation assay.

The results showed that, at a concentration of 10 ng/ml, the 3D6, 6G1 and 1A3.3.12 antibodies have some HGF agonistic effect. (See FIG. 2)

EXAMPLE 5

Anti-c-Met antibodies 05-237 and 05-238 (purchased from Upstate Biotechnology Inc., Lake Placid, N.Y.; see also, Prat et al., *Mol. Cell. Biol.*, suora, Prat et al., *Int. J. Cancer*, supra) and antibody 3D6 (described in Example 4) were tested and compared for their ability to induce DNA synthesis in a mink lung bioassay.

Mink lung cells (Mv 1 Lu, ATCC CC1 64) were passaged in DME/F12 (50:50) supplemented with 10% fetal bovine serum, penicillin, streptomycin and L-glutamine. Prior to conducting the bioassay, the mink lung cells were trypsinized, washed, and resuspended in assay medium (DME/F12 medium supplemented with 1 mg/ml BSA, penicillin, streptomycin and L-glutamine) to a concentration of $1 \times 10^5$ cells/ml. The bioassay was then conducted as described in Example 4.

Figure 3:
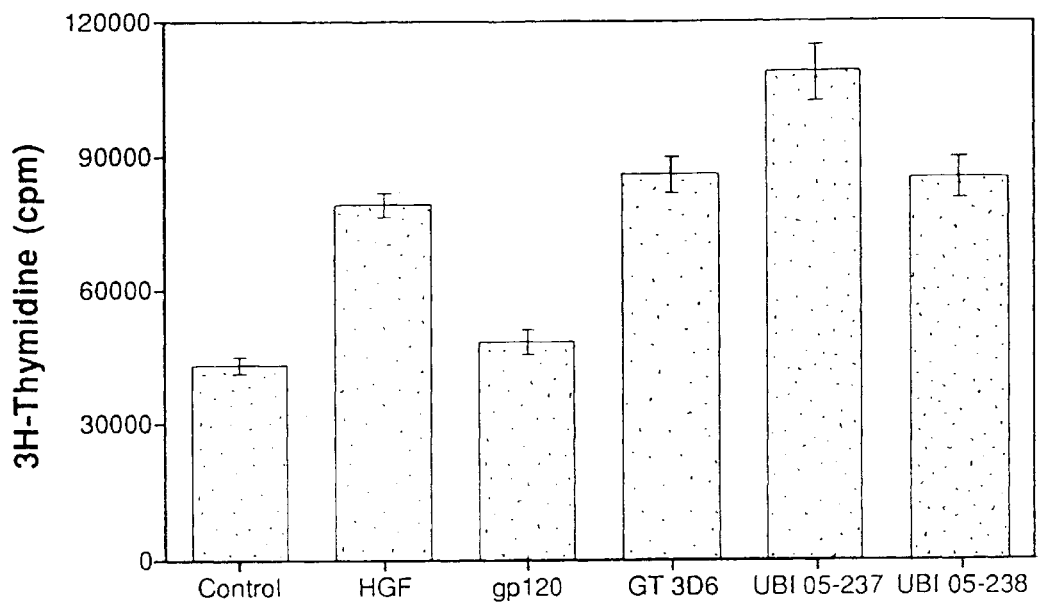
FIG. 3 is a bar diagram showing the stimulatory effect of monoclonal antibodies 3D6, 05–237 and 05-238 on mink lung cells in a proliferation assay.

The results showed that antibodies 05-237 and 05-238 have HGF agonistic effect. (See FIG. 3)

EXAMPLE 6

Antagonistic activity of 1A3.3.13 monoclonal antibody Fab fragments was determined using a thymidine incorporation assay. Monoclonal antibody 1A3.3.13 (described in Example 3) was digested with papain to obtain the Fab fragments. The papain digestion was performed by initially dialyzing the antibody against a 20 mM phosphate/10 mM EDTA, pH 7.0, buffer overnight. The antibody was then concentrated to approximately 10 mg/ml. Next, 0.5 ml immobilized papain (crosslinked 6% beaded agarose, obtained from Pierce Chemicals) was added to a 16×100 mm tube. The papain beads were washed 2 times with 4 ml of digestion buffer (42 mg cysteine-HCl in 12 ml phosphate buffer, pH 10). Each wash was removed using a separator. About 0.5 to 1 ml of the 1A3.3.13 antibody was added to the papain beads and then incubated in a heated shaker bath (37° C., 200 rpm) overnight. 1.5 ml of binding buffer (Immunopure IgG Binding Buffer obtained from Pierce Chemicals) was added to the tube, and the supernatant was separated from the beads with a separator. The supernatant was then passed over a Protein A column equilibrated with the binding buffer. Additional binding buffer was passed over the column and the eluate containing the Fab fragments was collected in 1 ml fractions. The fractions were analyzed by absorbance at 280 nm and the Fab containing fractions dialyzed against PBS overnight. Absorbance at 280 nm was read again to determine the concentration of Fab (about 1.53). The fractions were also run on a 7.5% SDS gel to determine the purity of the Fab in the fraction. The 1A3.3.13 Fab fragments were further tested in an inhibition assay (as described in Example 3). The Fab fragments did inhibit HGF binding but showed a weaker inhibitory effect as compared to intact 1A3.3.13 antibody (data not shown).

An expression plasmid was prepared by inserting a full-length cDNA for human c-Met (described as pOK met cDNA in Rodrigues et al., supra) into a pRK5.tk.neo vector [de Sauvage et al., *Nature*, 369:533–538 (1994); Gorman, *DNA Cloning: A New Approach*, 2:143–190 (IRL Washington 1985)]. The resulting plasmid was linearized and transfected into the IL-3 dependent cell line, BaF3 [Palacios et al., *Cell*, 41:727–734 (1985)] by electroporation (800 microfarad, 250 V, BRL electroporator). Selection of transfectants was performed by culturing the cells for 2–3 weeks in the presence of 2 mg/ml G418. One of the selected transfectant cell lines, referred to as BaF3-hmet.8, was confirmed by Western blotting to express c-Met. BaF3-hmet.8 also tested positive for response to HGF in a proliferation assay measuring incorporation of $^3$H-thymidine. Neither the parental BaF3 cells nor any cells derived by transfection with the pRK5.tk.neo vector alone were found to express c-Met or respond to HGF in the proliferation assay.

The BaF3-hmet.8 cells were passaged in RPMI medium supplemented with 10% fetal bovine serum, 5% WEHI-conditioned medium (as a source of IL-3) and 2 mM glutamine. Prior to conducting the assay, the cells were washed twice with assay medium (RPMI medium supplemented with 10% fetal bovine serum) and resuspended in assay medium to a concentration of $5 \times 10^4$ cells/ml. Next, 100 μl of the cells was added to each well in the 96-well culture plates. Various concentrations (0.2 μg/ml, 2 μg/ml, 20 μg/ml) of control gp 120 Fab fragments (gp 120 monoclonal antibody digested with papain as described above) and the 1A3.3.13 Fab fragments were prepared in assay medium and 100 μl was added to designated wells. The plates were incubated at 37° C. in 5% $CO_2$ for 15 hours.

One μCi $^3$H-thymidine was added to each well of the culture plates. The cells were harvested 7 hours later and the amount of radioactivity incorporated into the DNA was quantitated (CPM) in a microplate scintillation counter.

Figure 4:
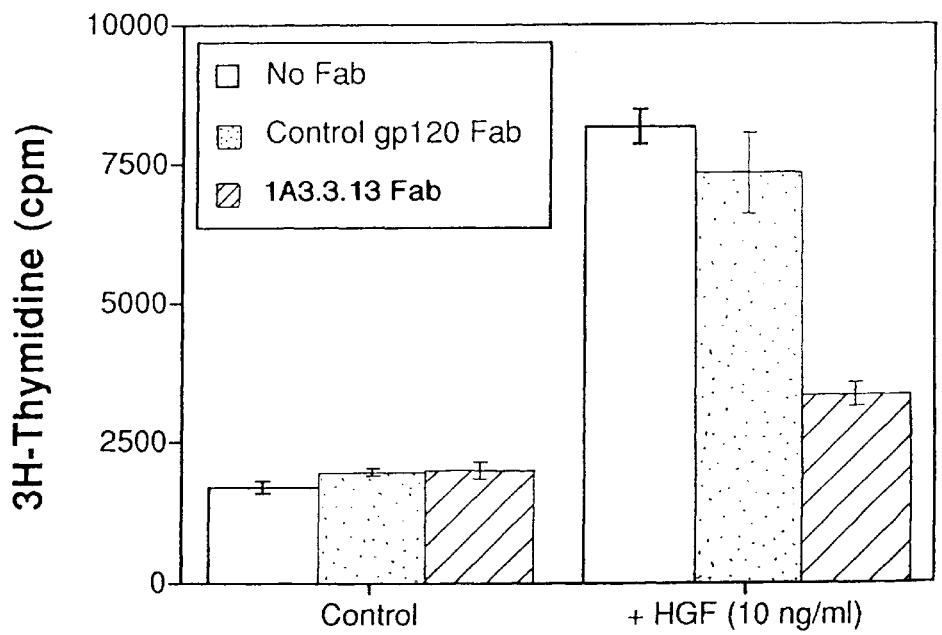
FIG. 4 is a bar diagram showing the inhibitory effect of monoclonal antibody 1A3.3.13 Fab fragments on BaF3-hmet.8 cells in a proliferation assay.

The results are shown in FIG. 4. At a concentration of 10 μg/ml, the 1A3.3.13 Fab fragments significantly blocked BaF3-hmet.8 cell proliferation in the presence of HGF.

Deposit of Materials

The following cultures have been deposited with the American Type Culture Collection, 12301 Parklawn Drive, Rockville, Md., USA (ATCC):

| Hybridoma | ATCC No. | Deposit Date |
|---|---|---|
| 1A3.3.13 | HB-11894 | May 23, 1995 |
| 5D5.11.6 | HB-11895 | May 23, 1995 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as an illustration of an aspect of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents.

What is claimed is:

1. A method of treating cancer in a mammal, comprising administering an effective amount of hepatocyte growth factor (HGF) receptor antagonist to a mammal diagnosed as having cancer, wherein said hepatocyte growth factor (HGF) receptor antagonist is an antibody.

2. The method of claim 1 wherein said cancer is breast cancer.

3. The method of claim 1 wherein said cancer is pancreatic cancer.

4. The method of claim 1 wherein said cancer is colon cancer.

5. The method of claim 1 wherein said cancer is lung cancer.

6. The method of claim 1 wherein said antibody is a monoclonal antibody.

7. The method of claim 1 wherein said antibody binds to the c-Met receptor.

8. The method of claim 7 wherein said antibody inhibits binding of human HGF to the c-met receptor.

9. The method of claim 1 wherein said antagonist is a Fab fragment of a monoclonal antibody.

10. The method of claim 6 wherein said monoclonal antibody is produced by the hybridoma cell line deposited under American Type Culture Collection Accession Number ATCC HB-11894.

11. The method of claim 6 wherein said monoclonal antibody is produced by the hybridoma cell line deposited under American Type Culture Collection Accession Number ATCC HB-11895.

12. An article of manufacture, comprising:
   a container;
   a label on said container; and
   a composition contained within said container;
   wherein the composition is effective for treating cancer, the label on said container indicates that the composition can be used for treating cancer, and the active agent in said composition comprises HGF receptor antagonist; and
   wherein said HGF receptor antagonist is an antibody.

13. The article of manufature of claim 12 further comprising instructions for administering the HGF receptor antagonist to a mammal.

14. A kit, comprising:
   a first container, a label on said first container, and a composition contained within said first container;
   wherein said composition is effective for treating cancer, the label on said first container indicates that said composition can be used for treating cancer, and the active agent in said composition comprises HGF receptor antagonist; and
   wherein said HGF receptor antagonist is an antibody;
   a second container comprising a pharmaceutically-acceptable buffer; and
   instructions for using said HGF receptor antagonist to treat cancer.

15. The method of claim 1, wherein said antibody is an antagonist for HGF that has the antigen binding ability of the hybridoma cell line deposited under American Type Culture Collection Accession Number ATCC HB-11894.

16. The method of claim 1, wherein said antibody is an antagonist for HGF that has the antigen binding ability of the hybridoma cell line deposited under American Type Culture Collection Accession Number ATCC HB-11895.

* * * * *

UNITED STATES PATENT AND TRADEMARK OFFICE
CERTIFICATE OF CORRECTION

PATENT NO. : 6,214,344 B1  
DATED : April 10, 2001  
INVENTOR(S) : Ralph H. Schwall et al.

Page 1 of 1

It is certified that error appears in the above-identified patent and that said Letters Patent is hereby corrected as shown below:

Title page,
Item [73] Assignee, correct the spelling of the Assignmsee from "Genetech, Inc." to -- Genentech, Inc. --.

Column 20,
Line 33, change "manfature" to -- manufacture --.

Signed and Sealed this

Fifth Day of February, 2002

Attest:

JAMES E. ROGAN
*Director of the United States Patent and Trademark Office*

*Attesting Officer*